United States Patent
Heyworth

(10) Patent No.: US 7,502,128 B2
(45) Date of Patent: Mar. 10, 2009

(54) MONITORING ARRANGEMENT FOR ROTATING COMPONENTS

(75) Inventor: Harold Heyworth, Loughborough (GB)

(73) Assignee: Rolls Royce, PLC, London (GB)

( * ) Notice: Subject to any disclaimer, the term of this patent is extended or adjusted under 35 U.S.C. 154(b) by 442 days.

(21) Appl. No.: 11/450,335

(22) Filed: Jun. 12, 2006

(65) Prior Publication Data

US 2007/0009252 A1    Jan. 11, 2007

(30) Foreign Application Priority Data

Jul. 8, 2005    (GB)    .................. 0514108.0

(51) Int. Cl.
   *G01B 11/14*    (2006.01)
(52) U.S. Cl. .................. 356/620; 356/614; 382/103
(58) Field of Classification Search .................. 356/614, 356/615, 620; 382/103
   See application file for complete search history.

(56) References Cited

U.S. PATENT DOCUMENTS

| | | | |
|---|---|---|---|
| 4,060,329 A | | 11/1977 | Ellis |
| 4,080,823 A | * | 3/1978 | Stargardter .................. 73/655 |
| 4,086,808 A | | 5/1978 | Camac et al. |
| 4,334,777 A | | 6/1982 | Bien et al. |
| 5,017,796 A | | 5/1991 | Makita |

FOREIGN PATENT DOCUMENTS

| | | |
|---|---|---|
| GB | 2 178 165 A | 2/1987 |
| JP | A 56-111407 | 9/1981 |
| JP | A 8-61917 | 3/1996 |
| WO | WO 92/22784 | 12/1992 |
| WO | WO 00/08415 | 2/2000 |

* cited by examiner

*Primary Examiner*—Roy M Punnoose
(74) *Attorney, Agent, or Firm*—Oliff & Berridge, PLC

(57) ABSTRACT

There are difficulties with regard to observing a rotating component in an obscuring environment such as typical of a gas turbine engine where there may be soot, flames, light signals and moisture. It will be understood that simply increasing the light intensity will increase scatter and therefore may "blind" a camera in terms of viewing distinctive features and targets within a rotating component. The present arrangement provides a mirror with an aperture such that an illuminating light source is directed towards a rotating component such that reflection is similarly incident upon the reflective mirror and light deflected to the camera. In such circumstances the camera is less susceptible to light scatter obscuration.

18 Claims, 5 Drawing Sheets

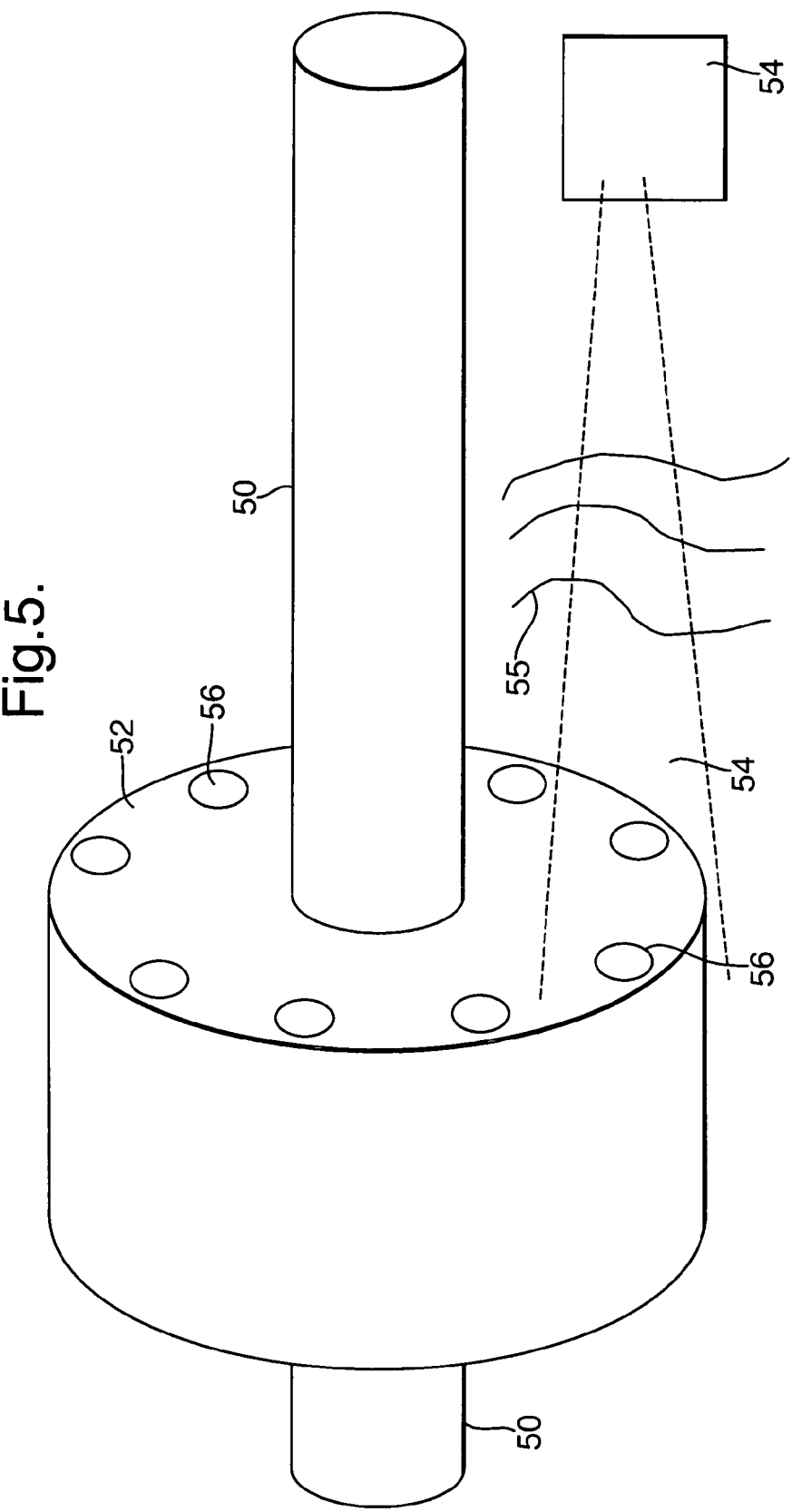

MONITORING ARRANGEMENT FOR ROTATING COMPONENTS

BACKGROUND OF THE INVENTION

The present invention relates to monitoring arrangements and more particularly to such monitoring arrangements utilised with regard to rotating components such as turbine blade assemblies in a gas turbine engine.

It is important to be able to monitor components such as rotating blade assemblies in order to determine distortion and deflection in that component during operational use.

It will be understood that rotating components will be subject to varying stresses and strains during use and therefore generally each of these components will distort and become displaced. A particular problem with respect to turbine blade assemblies in gas turbine engines is a so called blade-off situation where a blade becomes fully or partially detached or at least displaced causing rubbing with other components within the assembly. In such circumstances it is important to determine the varying distortions and displacements which precede such blade off situations in order that they can be avoided.

Previously the main means of monitoring a rotating component has been by simple observation. Thus, a camera will be mounted in an appropriate position relative to the rotating component in order to record its motion and then through subsequent replaying and observation distortions and displacements noted in the rotating component. It will be understood in order to highlight distortions and displacements typically a high intensity laser or other illumination source has been used in order to give high brightness and a narrow bandwidth light response. In such circumstances utilising a specially modified high-speed digital camera that generally only accepts or is biased towards the laser light bandwidth and rejects the background light emitted background it is possible to improve the accuracy of observations.

However, there are still particular problems from background or environmental light obscuring observations. This background light may be as a result of plasmas, arcs, flames and explosions typical in a gas turbine engine. It will also be understood that there may be dust or other particles which act as reflectors and so may further blind the camera in terms of its observational capacity.

In view of the above, previous methods are generally poor, and at least far from ideal, as it requires a high illumination level of light in order to indiscriminately penetrate the environmental pollution, that is to say, fog, dust, smoke, metallic and paint particles, soot, flames, water vapour, mist in the region in front of a rotating component such as a blade assembly in a gas turbine engine. However, a high illumination level can itself "blind" the camera by reflective light scatter from these particles. It would also be understood that there is lack of consistency in that the level of pollution which could cause camera blinding scatter may vary dependant upon operational state. In such circumstances it is not easy to provide any precision with regard to measuring displacement and distortion in the rotating component. Proposed attachment of high brightness devices to the rotating component will generally be unsatisfactory in that the device, that is to say a powered illumination source may be subject to breakage, provision of the device itself including its power supply will add to weight and therefore be intrusive with respect to a true response and may have limited effect upon the camera overall illumination.

SUMMARY OF THE INVENTION

In accordance with the present invention there is provided a monitoring arrangement for a rotating component, the arrangement comprising a target for association with the rotating component and target tracking apparatus comprising a camera to track the target to identify variations in the target and so the rotating component and a light source to illuminate at least the target; the arrangement characterised in that the camera and the light source are associated with a mirror with an aperture such that light projects through the aperture towards the target in use and light is reflected back from the target towards the mirror in use and deflected towards the camera in use for localised discrimination by the camera from general light background.

Typically, the mirror is arranged at forty-five degrees to the rotating component with the camera and the light source substantially perpendicular to each other about the aperture of the mirror. Normally, the mirror is a silvered or gold plate mirror.

Typically, the camera is a high-speed digital camera. Normally, the camera is associated with a lens combination for focusing deflected light from the mirror from the camera. Additionally, the arrangement normally incorporates a polariser.

Typically, the light source is a laser. Possibly, the light source is a high brightness narrow bandwidth laser. Possibly the light source has a specific wavelength for facilitating discrimination by the camera.

Possibly, the target is optically active. Advantageously the target is a retro reflector. Generally, the target will comprise a number of target elements for distribution about a component. Possibly, the target is a distinguishable feature in the rotating component.

Accordingly, another aspect of the present invention is a method of finding the off-set between a body's rotational axis and its nominal central axis, the body has disposed thereon at least two targets in known locations, the method comprising the steps of (a) rotating the body, (b) detecting the location of the two targets via a monitoring arrangement as described above, and (c) calculating the location of the rotational axis.

Preferably, the method comprises step (d) where the body is balanced by either adding or removing a mass to the assembly.

Preferably, the method includes the further step of repeating steps (a)-(c) to ensure the rotational axis and central axis of the body are coincident.

BRIEF DESCRIPTION OF THE DRAWINGS

Embodiments of the present invention will now be described by way of example and with reference to the accompanying drawings in which:—

DETAILED DESCRIPTION OF THE INVENTION

It is desirable to be able to monitor and review rotating components such as discs, hubs and fan blades within a gas turbine engine in order to denote variations in terms of displacement and distortion of the respective blades, discs or other parts within the component or the component itself.

Figure 1:
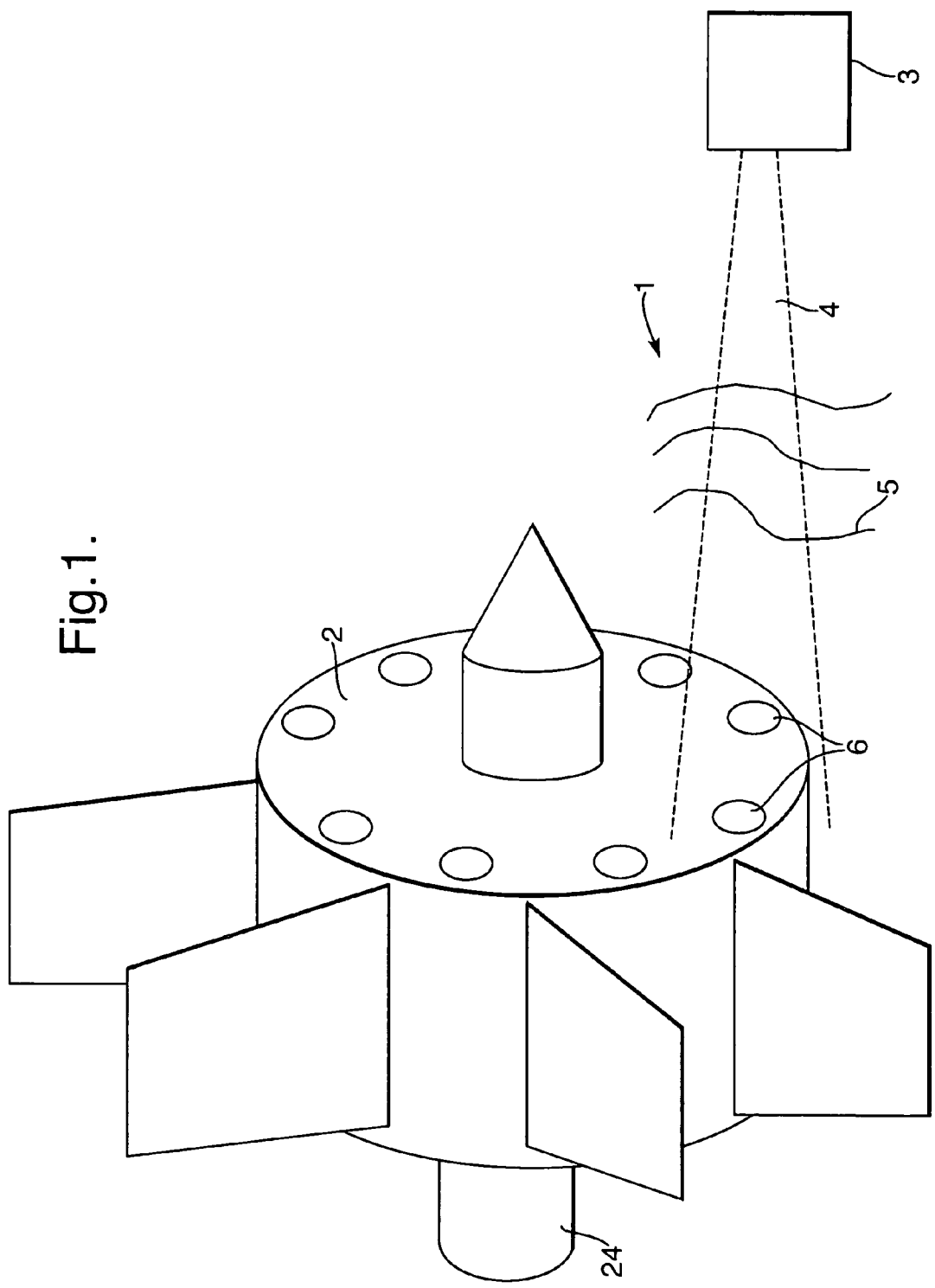
FIG. 1 is a schematic illustration of a monitoring arrangement in accordance with the present invention.

FIG. 1 provides a schematic illustration of a monitoring arrangement 1 in accordance with the present invention. Thus, a rotating component such as a fan disc 2 is viewed by a tracking apparatus 3 with an image 4 received from the component 2 through partial obscuration as a result of dust, flames light scatter etc. This partial obscuration is shown by lines 5 in FIG. 1. In order to enhance the accuracy of tracking typically targets in the form of retro reflectors 6 are secured to the rotating component 2.

The tracking apparatus 3 monitors the rotating component 2 and generates images 4 which are compared to determine variations in displacement as the components are subject to various operational conditions. This monitoring of the component 2 as indicated can be during prototyping and design stages for a machine incorporating the rotating components such as illustrated within a gas turbine engine incorporating the fan blades in an arrangement and a rotating component 2 depicted in FIG. 1. The clearer and more accurately the component 2 can be viewed the better the monitoring of that component. As indicated previously simply increasing light intensity is not appropriate as this may through polluting particles increase light scatter and the back ground light and therefore effectively blind the camera utilised within the tracking apparatus 3.

Figure 2:
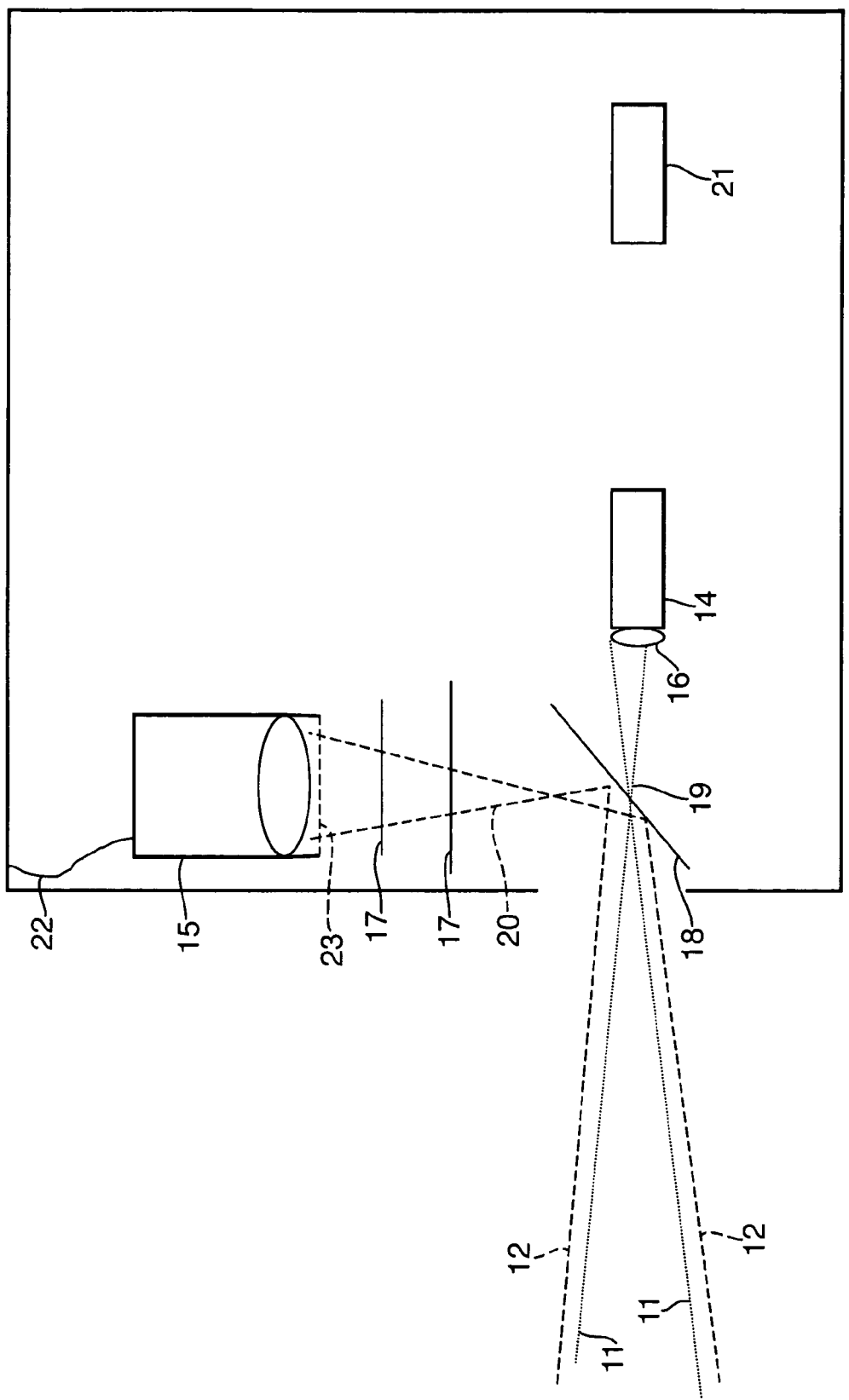
FIG. 2 is a schematic illustration of a target tracking arrangement in accordance with the present invention.

FIG. 2 provides a schematic illustration of a tracker apparatus 13 in accordance with the present invention. Thus, the apparatus 13 incorporates a light source in the form of a laser 14 and a high-speed digital camera 15. The light source incorporates a lens 16 to project light towards a mirror 18 with an aperture 19. The camera 15 is associated with a filter and polariser combination 17 in order to appropriately present an image 20 to the camera 15. It will also be understood that the laser 14 is associated an appropriate power source 21 whilst the camera 15 will be associated through a cable 22 with a controller whereby the images will be stored and compared as described later as well as provide for adjustment of the camera 15 made in order to achieve best results. Generally the camera 15 is a high-speed digital camera with or without frame synchronised output. Additionally, a high-speed shutter 23 may be used to improve image quality by opening and closing in conjunction with a pulsed light beam and thereby reducing background noise. The light source as indicated is normally a laser 14 which is divergent and may provide a continuous or pulsed light beam. Other laser types may be used to reduce back scatter. With laser choice dependant on wavelength and particle size. In a preferred embodiment, as indicated a light filter and polariser combination 17 is provided which matches with the laser wave length light source 14 as described above. As indicated previously in order to enhance discrimination from background typically targets in the form of retro reflectors 6 (FIG. 1) will be utilised in the present arrangement. These targets may be provided with a protective surface feature if required. Furthermore, where possible these targets may be designed for enhanced reflection at the wavelength of the light source 14. Camera images are relayed and stored in an appropriate storage facility of a controller for subsequent study. This may be through comparison of images. It may also be possible to provide determinations as to calculate fan orbit centre when it is difficult to find the centre of a rotating component. It should be appreciated that the retro-reflector 6 substantially reflects light back towards the light source, however a small angular deviation is necessary to avoid all the reflected light returning through the aperture 19 in mirror 18.

The use of an aperture 19 in the mirror 18 is preferred over a beam-splitter arrangement that could be placed in this position. This is due to the beam-splitter arrangement allowing a high level of background light to pass into the camera, which gives problems in separating the background laser light from the return laser light. Additionally the aperture in the mirror greatly aids maximising the light return from the retro-reflector to the camera. This is due to the return beam being slightly deviated by: a) lateral displacement of the return beam due to its path in the retro-reflector; b) diffraction caused by the finite aperture of the retro-reflector and the wavelength of light used and c) the imperfect build quality of the retro-reflector. This leads to the return of a high proportion of the light emitted by the laser being returned to a region around the aperture in the mirror and thereon being reflected towards the camera. If it where not for these deviations then the return signal would pass back down the aperture and no light signal from the retro-reflector would be detected. The overall effect being that there appears to be very high brightness light sources emanating from the object.

In general operation in accordance with the present arrangement light is emitted from the light source laser 14 and passes through the aperture hole 19 in the mirror 18 tilted appropriately. On account of the expansion caused by a lens in front of the laser 14, a patch of light shown by first broken line 11 is incident upon the rotating component, that is to say a fan blade assembly. This incident light is reflected typically at least from the target reflectors 6 (FIG. 1). The reflected light impinges upon the mirrored surface of the mirror 18 and in deflected towards the camera 15. The deflected light enters the lens of the camera and is focused on an image detector. The images from the detector are stored in an appropriate controller as described later until such a time as they can be analysed. Analysis consists partly of a mathematical routine to extract the co-ordinates of the points of interest, i.e. the known feature positions, and relate them to the centre of orbit of the subject rotating component.

The present arrangement allows identification of a rotating component orbit centre under very difficult, that is to say high light attenuation circumstances. By the effective use of a low divergence typically laser light signal, retro reflectors and the apertured mirror 18, it is possible to allow a high brightness signal to be captured by the camera 15 as the camera is not swamped and blinded by any scattered or background light. By such provision the present arrangement ensures a high signal to noise ratio over any background reflection or light signals from such sources as flames about a rotating component such as a blade assembly in a gas turbine engine.

In situations where the centre of rotation is not accessible it is possible that multiple retro-reflectors will allow calculation of the rotating component dimensions by consideration of successive images received by the camera 15. However where accessibility is not a problem it may be possible to provide a situation where a single target in the form of a reflector could be fitted to the centre of the rotating component to act as a reference for image analysis. It will be understood that the retro reflected high intensity light beam from the laser 14 should be sufficient to overcome any large attenuation through dust or otherwise between the rotating component and the tracking apparatus. It will be understood that the targets 6 in accordance with the present invention are passive and will therefore not require a power source. In such circumstances the targets 6 will cause minimum additional weight and therefore will be less intrusive with regard to the results to be achieved. The use of several targets allows observation by image analysis and calculation of disc/object centres. As indicated previously through a known mathematical routine it is possible to calculate the centre of orbit of the rotating component. (If there are two or more known target positions).

As indicated above light from laser 14 is projected through the aperture 19 towards a rotating component in a beam defined by first broken lines 11. Some reflected light from the rotating component and from at least two of the targets, that is to say retro-reflectors 6 is returned to the tracking apparatus 13 along the path defined by second broken line 12. This reflected light 12 is itself reflected and deflected by the mirror 18 towards the camera 15 through the filter and polariser combination 17. The image is then recorded by the camera 15 and stored appropriately.

The mirror 18 is tilted and is generally at substantially forty-five degrees to the front of the rotating component. In such circumstances the light source laser 14 and camera 15 are then substantially in a perpendicular relationship about the aperture 19. Clearly, other optical angular presentations of the components may be achieved but will require active lens or other deflection mechanisms which may diminish light intensity particularly at optical interfaces and therefore capacity for high resolution. A beam splitter is not recommended for the reasons as hereinbefore described.

By use of the mirror 18 and normally the filter/polariser combination 17, it will be appreciated that local discrimination with regard to the image is achieved such that light scatter will not blind or over-expose the camera in terms of sensitivity or resolution.

The targets in the form of retro reflectors may be discrete components or specifically cut from a sheet of retro-reflective material and associated with the rotating component, or may even be for instance drilled bolt heads that perform the retro-reflection function. As indicated the light source laser may be continuous or pulsed to allow synchronisation to or with the camera in capturing images.

As indicated above in accordance with the present arrangement the target is utilised in order to provide a reference within the image for comparison. In such circumstances the present arrangement can be utilised wherever there is a recognisable target feature for such image to image correlation. The arrangement has particular applicability where there is a poor transmissive medium such as through soot or dust or flame light signals, each of which are typical within a gas turbine engine, but where it is desirable to monitor a rotating component. In such circumstances the present arrangement has particular capability with respect to monitoring gas turbine engines either in prototype or service mode. Furthermore, as will be described later, it is possible to monitor these deflections relative to another reference such as a wing or fuselage position. Additionally, where multiple targets are available and used as indicated above it is possible to monitor wheel rotation, on or off axis, as the centre of rotation of the rotation device and deflection from the expected rotational centre and this can be utilised in order to determine the deflection on aircraft or road vehicles for either safety or design data assessment.

The present arrangement has no direct contact with the rotating component and therefore can be considered non intrusive. If the centre of rotation is not directly available as the shaft exits on that centre of rotation the present arrangement may be used as an aid to shaft alignment. Furthermore, where a disc or partial disc has slid down a rotational shaft it will be appreciated that the present arrangement allows the position of the shaft centre to be found greatly aiding alignment of shafts in dirty or otherwise obscuring environments.

Figure 3:
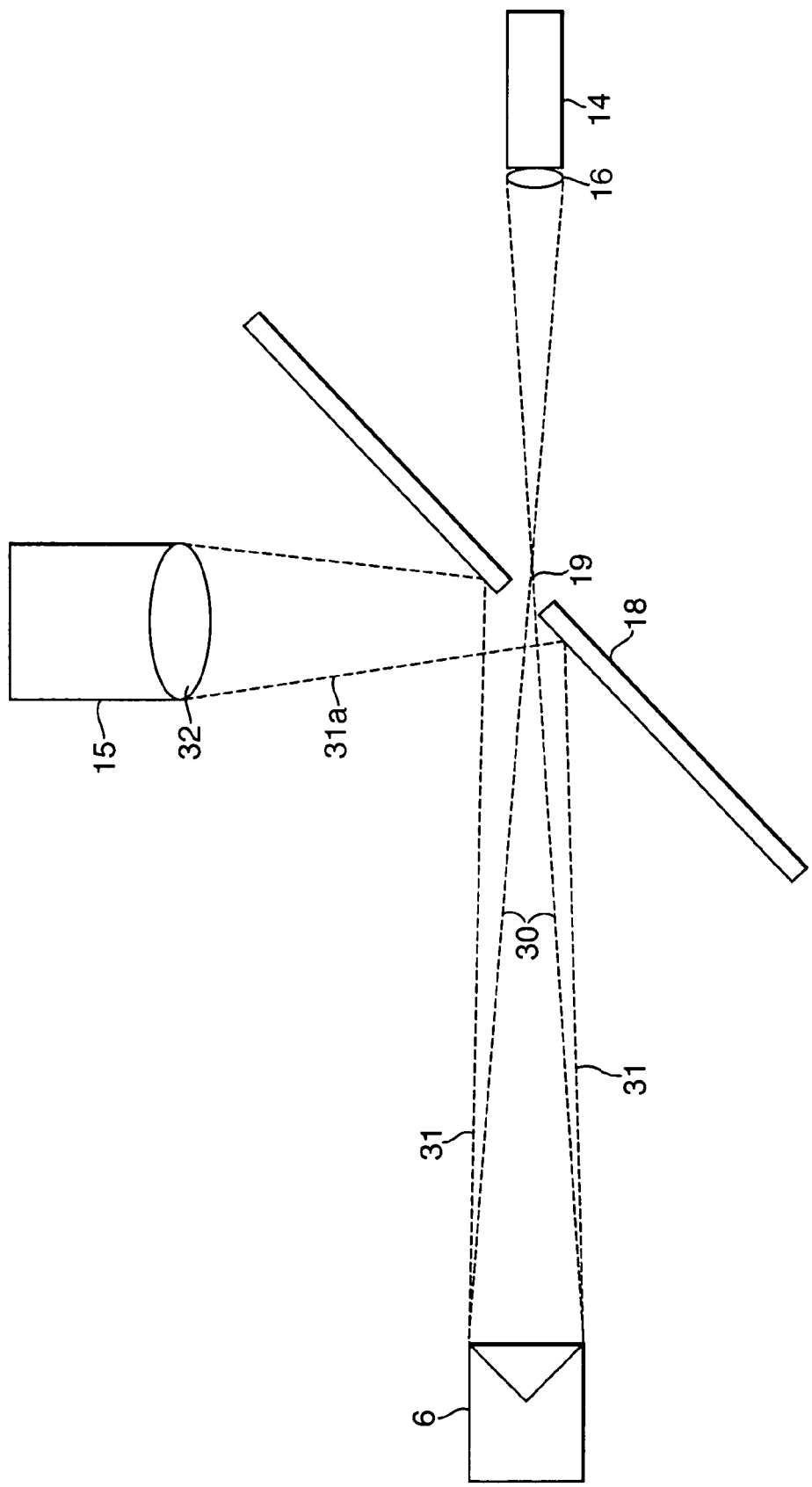
FIG. 3 is a schematic illustration showing light paths in accordance with the present invention.

FIG. 3 provides a schematic illustration of the optical paths in accordance with the present arrangement. Consistent reference nomenclature to FIG. 2 has been used for clarity. Thus, a light source 14 in the form of a laser is associated with the lens 16 in order to project an expanded light beam 30 towards a target retro reflector 6 (FIG. 1) and light is then reflected back along optical path 31 to become incident upon the mirror 18. The mirror 18 comprises a silvered plate such that the reflected light beam 31 is then deflected in the direction 31a to become incident upon the camera 15 through its lens 32. The camera 15 captures an image and this is stored as described above and used for comparison. The laser 14 may provide a continuous or pulsed light beam such that the camera 15 acquires images at different time periods as defined by a timer if the light beam is continuous or captures images for each light beam pulse from the laser 14. A single retro reflector is illustrated in FIG. 3 but it would be appreciated that normally a rotating component will include a number of such reflectors to be deduced in the image captured by the camera 15 for analysis.

Figure 4:
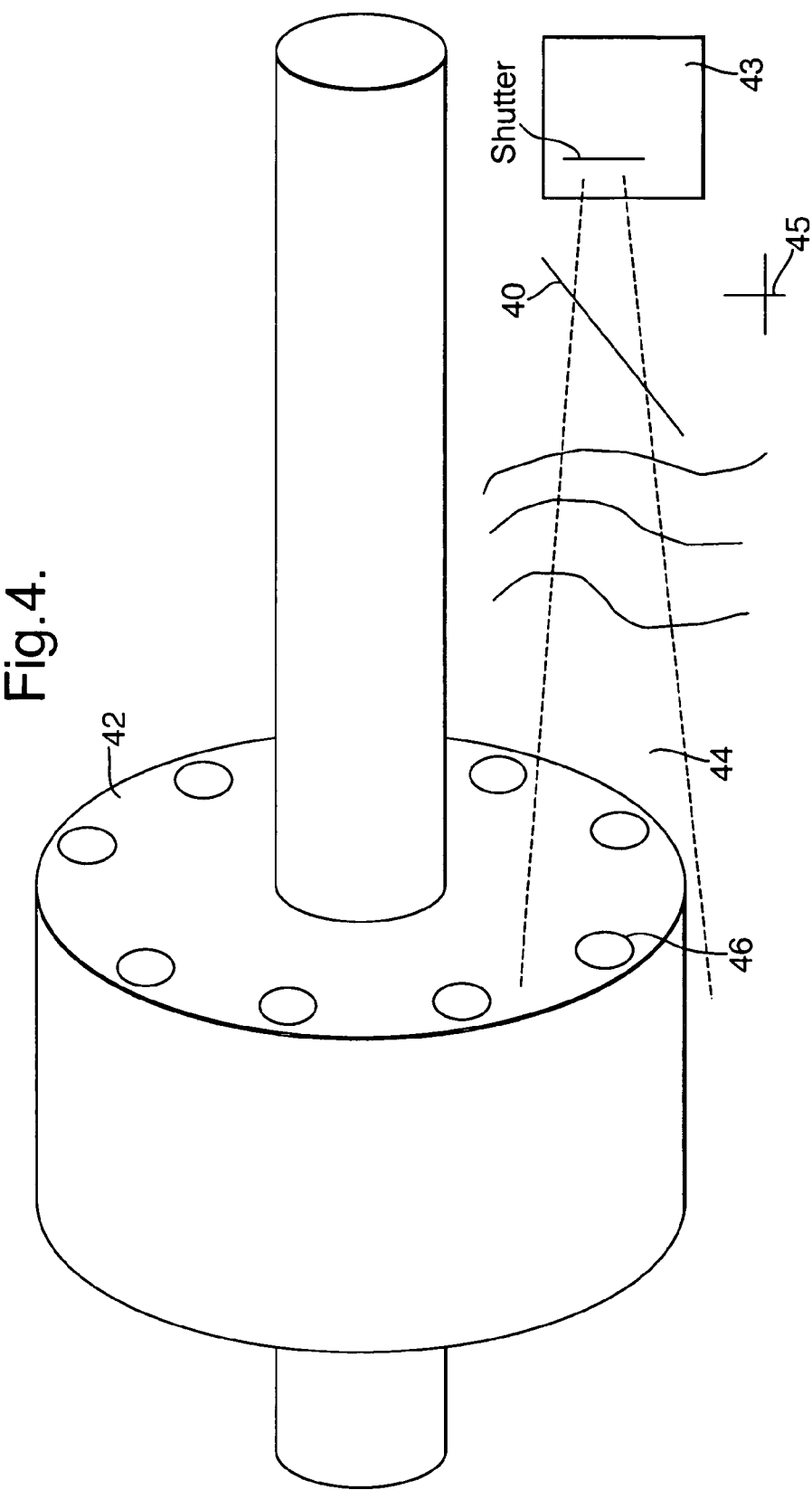
FIG. 4 schematic illustration of a refinement to the present monitoring arrangement incorporating a reference point or area; and, FIG. 5 is a schematic illustration of a further refinement of the monitoring arrangement described above.

As indicated above where a centre of rotation cannot be utilised as a reference alternatives may be used. Thus, as illustrated in FIG. 4, an additional partial transmitting/reflective plate 40 may be placed at the entrance to a tracker apparatus 43. If the plate 40 is sufficiently tilted it can allow a reference target 45 to be observed coincidentally with a retro reflected signal 44 from a rotating component 42. In such circumstances the reference point 45 will be shown in the image and utilised for reference with regard to other identifiable features in the image. It will be understood that the reference point should be accurately calibrated relative to the rotating component 42, but in any event will generally be stable in comparison with the rotating component 42. An example of utilisation of this refinement to the present arrangement would be to observe a position upon the ground adjacent the rotary component to ensure a reference for any observed movement in the rotatable component 42.

As indicated above generally a rotating component will have a number of targets or distinctive features in the form of retro reflectors. Thus, as illustrated in FIG. 5, a rotating component 52 is secured upon a shaft 50 in order to rotate. A number of targets 56 are secured to the rotating component 52. Thus, if there is a dusty environment 55 obscuring an image 54 received by a tracker apparatus 53 it will be understood that as the position of the targets 56 is known it will still be possible to identify movements and deflections in the shaft 58 in terms of centre of rotation for the rotating component 52 as well as with regard to other distortions provided these retro reflectors can still be identified in the image captured by the camera in the tracker apparatus 54.

A shutter associated with the camera gives an advantage for the following reasons. When used with a pulsed light source it prevents the camera acquiring spurious and unnecessary light signals. The shutter being synchronised with the pulsed laser and or the camera. Such shutters may be any one of mechanical, electronic or as known to the skilled artisan. (see FIG. 4).

Modifications and alterations to the present monitoring arrangement will be understood by those skilled in the art. Thus it will be appreciated that the rotating component in accordance with the present invention may be associated with targets such that movement of the rotating component to locate shaft centres as a function of axial position will not affect the ability of the monitoring arrangement to deduce displacements and distortions provided there is adequate reflection from the targets to allow capture of images by the camera. It will be understood that general operation of the present arrangement will ensure that the captured images from the camera are transferred to an appropriate controller and processor such that images can be compared in terms of position of targets and other distinct features in the rotating component in order to monitor that component.

The present invention is also embodied by a method of calculating the co-ordinates of the centre of rotation of a body 2, 24 (such as the joined disc 2 and shaft 24 arrangement in FIG. 1) and thus an off-set between a body's 2, 24 rotational axis and its nominal central axis. This is particularly useful when the shaft 24 rotational axis itself is unobservable, for example when in use. An array of retro-reflectors 6 is placed on the disc 2, to which the shaft 24 is attached in known positions relative to the nominal central axis. In this example if at least two retro-reflector 6 positions are known and the angle between them is known (about the nominal physical central axis of the shaft 24) then by simple trigonometry and knowledge of the radii lengths a position in terms of x_and y co-ordinates can be found for the centre of rotation by solving a quadratic equation. The x and y coordinates are relative to the bottom left hand side of the camera image but any notional datum or reference position may be used.

Thus before rotation the position of the nominal physical axis of the disc/shaft is known; then during operation, the disc/shaft rotates about an actual rotational axis which is then observed by the monitoring arrangement as hereinbefore described, and the new locations of the two retro-reflectors can be measured and using simple trigonometry the centre of rotation of the shaft may be calculated. This method is therefore useful for balancing rotor assemblies, the method further comprising balancing the rotor by either adding or removing a mass to the assembly and re-calculating the centre of rotation. Other known methods of balancing may be used.

Knowing the centre of rotation and in association with time data it is possible to ascertain the accelerations and hence loads imposed on the structure of the engine and to determine what loads are passed through to the pylon/wing.

I claim:

1. A monitoring arrangement for a rotating component, the arrangement comprising a target for association with the rotating component and target tracking apparatus comprising a camera to track the target to identify variations in the target and so the rotating component and a light source to illuminate at least the target; the arrangement characterised in that the camera and the light source are associated with a mirror with an aperture such that light projects though the aperture towards the target in use and light is reflected back from the target towards the mirror in use and deflected towards the camera in use for localised discrimination by the camera from general light background.

2. An arrangement as claimed in claim 1 wherein the mirror is arranged at forty-five degrees to the rotating component with the camera and the light source substantially perpendicular to each other about the aperture of the mirror.

3. An arrangement as claimed in claim 1 wherein the mirror is any one of the group comprising silvered or gold plate mirror.

4. An arrangement as claimed in claim 1 wherein the camera is a high-speed digital camera.

5. An arrangement as claimed in claim 1 wherein the camera is associated with a lens combination for focusing deflected light from the mirror from the camera.

6. An arrangement as claimed in claim 1 wherein the arrangement normally incorporates a polariser.

7. An arrangement as claimed in claim 1 wherein the light source is a laser.

8. An arrangement as claimed in claim 7 wherein the light source is a high brightness narrow bandwidth laser.

9. An arrangement as claimed in claim 1 wherein the light source has a specific wavelength for facilitating discrimination by the camera.

10. An arrangement as claimed in claim 1 wherein the target is optically active.

11. An arrangement as claimed in the claim 10 wherein the target is a retro reflector.

12. An arrangement as claimed in the preceding claim 11 wherein the target will comprise a number of target elements for distribution about a rotating component.

13. An arrangement as claimed in the preceding claim 12 wherein the target comprises an identifiable feature in a subject rotating component.

14. A gas turbine engine associated with a monitoring arrangement for monitoring a rotating component within the gas turbine engine, the monitoring arrangement being as claimed in claim 1.

15. An engine as claimed in claim 14 wherein the rotating component is a turbine blade assembly.

16. A method of finding the off-set between a body's rotational axis and its nominal central axis, the body (has disposed thereon at least two targets in known locations, the method comprising the steps of (a) rotating the body, (b) detecting the location of the two targets via a monitoring arrangement of claim 1, and (c) calculating the location of the rotational axis.

17. A method according to claim 16 wherein the method comprises step (d) where the body is balanced by either adding or removing a mass to the assembly.

18. A method according to claim 17 wherein the method includes the further step of repeating steps (a)-(c) to ensure the rotational axis and central axis of the body are coincident.

* * * * *